June 24, 1958 W. B. MOONEY Plant Pat. 1,721
APPLE TREE
Filed Oct. 17, 1957
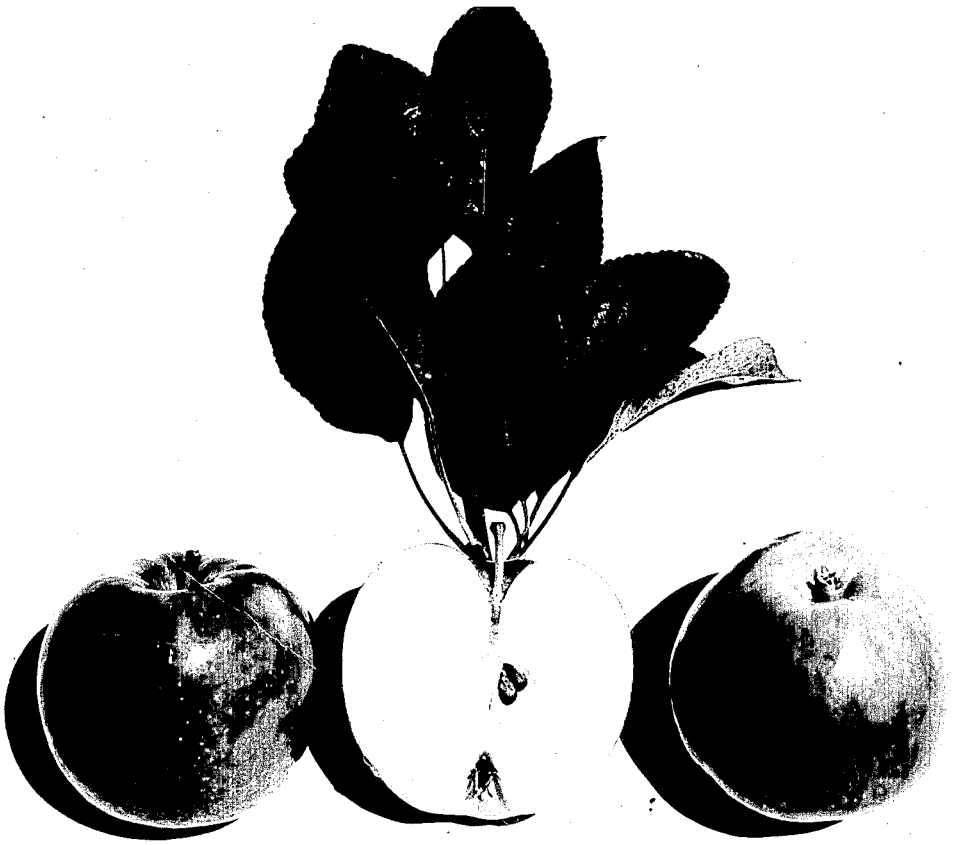
INVENTOR
W. B. Mooney, Deceased
By: Mabel Ruth Runty, Executrix.
BY
Robb & Robb ATTORNEYS United States Patent Office Plant Pat. 1,721
Patented June 24, 1958

1,721

APPLE TREE

Worth B. Mooney, deceased, late of New Lenox, Ill., by Mabel Ruth Runty, executrix, Manhattan, Ill., assignor to Stark Bro's Nurseries and Orchards Company, Louisiana, Mo., a corporation of Missouri Application October 17, 1957, Serial No. 690,882

1 Claim. (Cl. 47—62)

The present invention relates to a new and distinct variety of apple tree which was discovered by the late Worth B. Mooney as a newly found seedling on cultivated property owned by him in New Lenox Township, Will County, Illinois.

At the time of his discovery, his attention was attracted to the new variety by the fact that it was growing in a fence row, and bore more highly colored fruit than that of any other variety then being cultivated by him. He thereupon took steps to preserve the originally-discovered plant, keep it under observation and to later asexually reproduce the same. These observations and asexual reproductions, as performed by grafting at Louisiana, Pike County, Missouri, conclusively established that the new variety bears fruit of substantially the same size and has substantially the same ripening season as the variety "Wealthy" (unpatented), but that the fruit has a more attractive and uniform red color, is more tapering in form, with a more conic calyx tube, more conspicuous dots on the fruit skin, more even in its ripening habit, and the fruit has firmer flesh and a much better flavor than that of the "Wealthy" variety aforesaid.

While the actual parentage of the new variety is not known, it is definitely differentiated from all other varieties of which he was aware, and the characteristics mentioned in the foregoing represent a unique and desirable combination which is particularly valuable from a commercial standpoint.

The accompanying drawing shows typical specimens of the fruit of the new variety, as depicted in color as nearly true as it is reasonably possible to make the same in a color illustration of this character, certain of said specimens depicting the exterior shape and coloring of the fruit, while another specimen shows a cross-section to expose the interior details thereof.

The following is a detailed description of his new variety, with color terminology in accordance with Ridgway's Color Standards and Nomenclature, and with the Horticultural Colour Guide, as indicated, except where general color terms of ordinary dictionary significance are obvious:

(Observations made from specimens grown at Louisiana, Missouri.)

Dates first and last pickings—from about August 6th to about August 15th; usually ripens at about the same season as "Wealthy."

Tree: Medium large; medium vigorous; upright; tall; vase-formed; rapid-growing; hardy; productive; regular bearer.

*Trunk.*—Medium stocky; smooth.

*Branches.*—Medium thickness; smooth; much-branching. Color—Liver Brown, Plate XIV, Color No. 7', tone M (Ridgway).

*Shoots.*—Color—Hays Maroon, Plate XIII, Color No. 1', tone M (Ridgway). Lenticels—numerous; large.

*Leaves.*—Length about 3¼ inches; width about 1⅞ inches; medium large; medium narrow; medium length; oval; taper-pointed; medium thickness; from smooth to slightly rugose. Color—Ivy Green, Color No. 0001060/2, page 200, vol. 2 (Horticultural Colour Guide). Margin—crenate. Petiole—Medium length (about 1⅛ inches); medium thickness.

Flowers: Medium early; large.

*Color.*—White, with tinge of Spirea Red, Plate 025/3, page 112, vol. 2 (Horticultural Colour Guide) on lower surface of some petals.

*Date of first bloom.*—About April 15th.

*Date of full bloom.*—About April 22nd.

Fruit:

*Maturity when described.*—Eating ripe.

*Size.*—Uniform. Axial diameter—about 2½ inches. Transverse diameter—about 3 inches.

*Form.*—Truncate at base; round conic.

*Cavity.*—Symmetrical; rounded toward apex; acute; undulate. Depth—about ⅝ inch. Breadth—about 1 inch.

*Markings.*—Color—Willow Green, Plate 000862/1, page 199, vol. 2 (Horticultural Colour Guide).

*Basin.*—Symmetrical; abrupt at base; wide furrowed; glabrous. Depth — about ¼ inch. Breadth—about ⅞ inch.

*Stem.*—Medium slender; pubescent; no markings. Length—about 15/16 inch. Breadth—about 5/32 inch.

*Calyx.*—Closed. Segments — persistent; broadly lanceolate; obtuse; about ¼ inch long; approximate at base; ascending; reflexed from base at apex; both outer and inner surfaces pubescent.

*Skin.*—Thin; tough; smooth; glossy; waxed. Dots—obscure; many; small; depressed; circular. Color—white; distribution—even, except few toward base and apex. Ground color—Chartreuse Green, Plate 663/1, page 90, vol. 1 (Horticultural Colour Guide). Color markings—striped; bright; Claret Rose; Plate 022/2, page 110, vol. 2 (Horticultural Colour Guide), with Chrysanthemum Crimson streaks, Plate 824/2, page 169, vol. 2 (Horticultural Colour Guide).

*Bloom.*—Wanting.

*General color effect.*—Red.

*Flesh.*—Rather juicy. Color—satiny white, with greenish tint. Texture—firm; fine; crisp. Flavor — sprightly; sub-acid. Aroma — distinct. Quality—good.

*Core.*—Sessile. Bundle area—small; narrowly ovate; unsymmetrical; in bundles opposite and alternate with cell. Halves of core—unequal. Bundles—inconspicuous; in one whorl; color—Chartreuse Green, Plate 663/2, page 90, vol. 1 (Horticultural Colour Guide). Core lines—clasping; indistinct in cross section. Carpellary area—indistinct; small. Calyx tube—pubescent toward base; broadly cone-shaped; entire depth about ¼ inch. Styles—present; united toward base; pubescent toward base. Stamens—one whorl; basal. Seed cells—axile; closed; cell walls—approximate; thin; tough; from broadly oval to orbicular; obtuse at apex; length—about 11/16 inch; breadth—about ⅜ inch; surface—fissured; medium narrow.

Seeds:

*Number.*—9 or 10 perfect; none imperfect; no more than 2 per cell.

*Length.*—About ⅜ inch.

*Breadth.*—About 3/16 inch.

*Form.*—Acute.

*Color.*—Chestnut, Plate II, Color No. 9, tone M (Ridgway).

Use: Market; culinary.

Keeping quality: Medium good.

He claims:

A new and distinct variety of apple tree, substantially as herein shown and described, characterized particularly as to novelty by its fruit which has substantially the same size and ripening season as the variety "Wealthy" (unpatented), but said fruit being distinguished from that of the variety "Wealthy" by a more attractive and uniform red color, a more tapered form, a more conic calyx tube, more conspicuous dots on the fruit skin, being more even-ripening, with firmer flesh and a much better flavor.

No references cited.